(12) United States Patent
Khanuja et al.

(10) Patent No.: US 7,235,262 B2
(45) Date of Patent: Jun. 26, 2007

(54) **USE OF BIOACTIVE FRACTION FROM COW URINE DISTILLATE ('*GO-MUTRA*') AS A BIO-ENHANCER OF ANTI-INFECTIVE, ANTI-CANCER AGENTS AND NUTRIENTS**

(75) Inventors: Suman Preet Singh Khanuja, Lucknow (IN); Sushil Kumar, Lucknow (IN); Ajit Kumar Shasany, Lucknow (IN); Jai Shankar Arya, Lucknow (IN); Mahendra Pandurang Darokar, Lucknow (IN); Monika Singh, Lucknow (IN); Prachi Sinha, Lucknow (IN); Soumya Awasthi, Lucknow (IN); Subhash Chandra Gupta, Lucknow (IN); Vivek Kumar Gupta, Lucknow (IN); Madan Mohan Gupta, Lucknow (IN); Ram Kishore Verma, Lucknow (IN); Sweta Agarwal, Lucknow (IN); Sunil Balkrishna Mansinghka, Maharashtra (IN); Suresh Haribhau Dawle, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 435 days.

(21) Appl. No.: 10/822,790

(22) Filed: Apr. 13, 2004

(65) Prior Publication Data

US 2005/0100610 A1 May 12, 2005

Related U.S. Application Data

(62) Division of application No. 10/135,763, filed on May 1, 2002, now Pat. No. 6,896,907, which is a division of application No. 09/726,307, filed on Dec. 1, 2000, now Pat. No. 6,410,059.

(60) Provisional application No. 60/241,842, filed on Oct. 20, 2000.

(51) Int. Cl.
*A61K 35/22* (2006.01)
(52) U.S. Cl. .................................. 424/558
(58) Field of Classification Search .................. None
See application file for complete search history.

(56) References Cited

U.S. PATENT DOCUMENTS

| 6,231,849 B1 * | 5/2001 | Schiller | 424/84 |
| 6,887,974 B2 * | 5/2005 | Pathak | 530/200 |

* cited by examiner

*Primary Examiner*—Michael Meller
(74) *Attorney, Agent, or Firm*—Buchanan, Ingersoll & Rooney, PC

(57) ABSTRACT

The invention relates to a novel pharmaceutical composition comprising an effective amount of bio-active fraction from cow urine distillate as a bioavailability facilitator and pharmaceutically acceptable additives selected from anticancer compounds, antibiotics, drugs, therapeutic and nutraceutic agents, ions and similar molecules which are targeted to the living systems.

4 Claims, 1 Drawing Sheet

Figure 1:
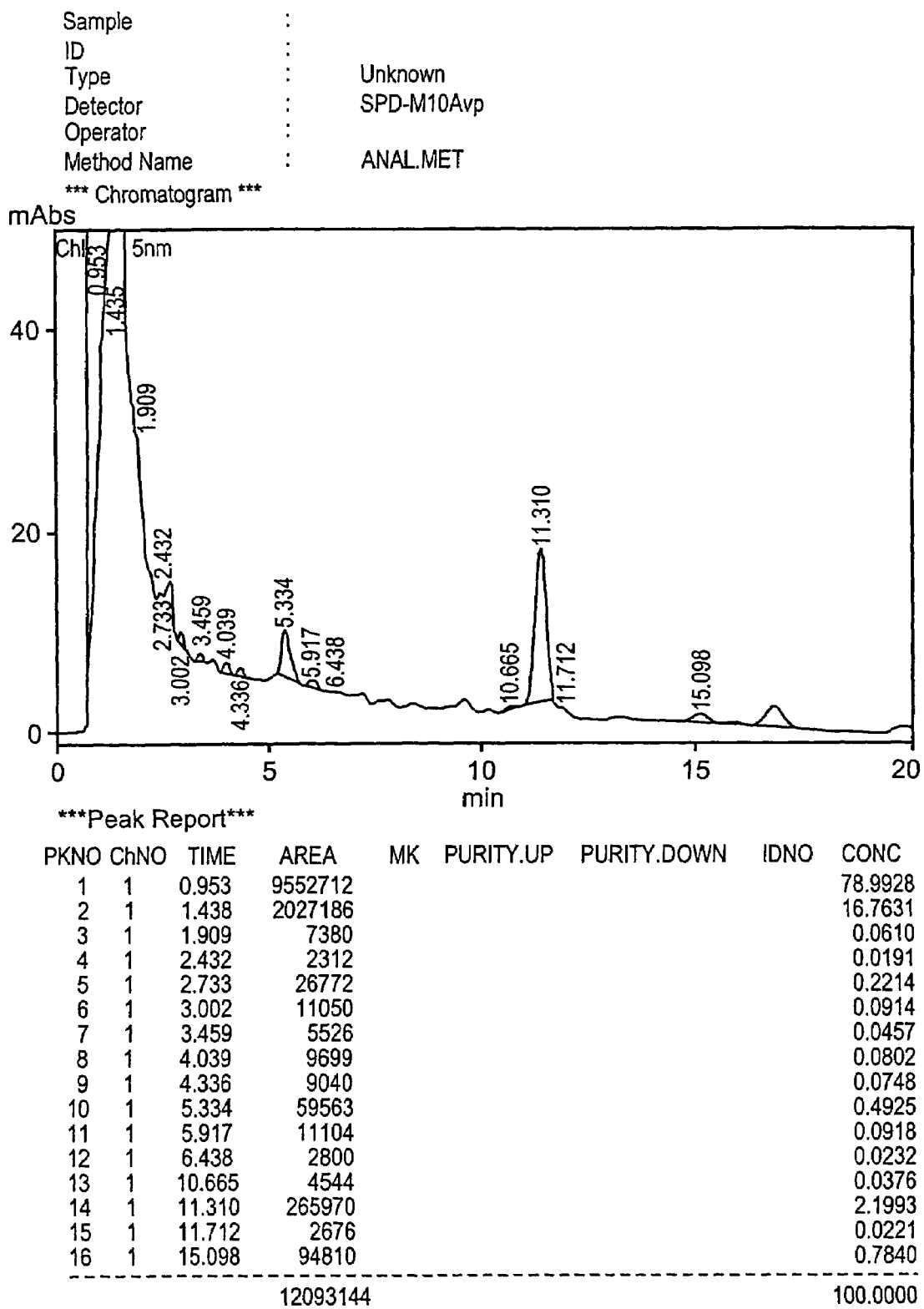

USE OF BIOACTIVE FRACTION FROM COW URINE DISTILLATE ('GO-MUTRA') AS A BIO-ENHANCER OF ANTI-INFECTIVE, ANTI-CANCER AGENTS AND NUTRIENTS

This application is a divisional, of application Ser. No. 10/135,763, filed May 1, 2002, now U.S. Pat. No. 6,896,907 which is a divisional of application Ser. No. 09/726,307, filed Dec. 1, 2000, now U.S. Pat. No. 6,410,059. issued Jun. 25, 2002, which are both hereby expressly incorporated by reference in their entirety.

This application claims priority under 35 U.S.C. §§ 119 and/or 365 to 60/241,842 filed in the U.S. on Oct. 20, 2000; the entire content of which is hereby incorporated by reference

FIELD OF THE INVENTION

The invention relates to an absolutely novel use of cow urine distillate as activity enhancer and availability facilitator for bioactive molecules including anti-infective and anti-cancer agents. The molecules which express any activity in form of either inhibiting or promoting a biological function have been referred in this invention as bioactive molecule e.g. antibiotics, drugs, nutraceuticals, cardiovascular, hepatoprotective, neuro-tonics etc. The present invention has direct implication in drastically reducing the dosage of antibiotics, drugs and anti-cancer agent while increasing the efficiency of absorption of bioactive molecules.

BACKGROUND OF THE INVENTION

In Ayurveda cows urine is suggested for improving general health. But it is never scientifically tested for any utility alone. The applicants have developed the curiosity about this component in the preparations and asked many questions to them; whether the component cow urine is having any activity by itself or it does not have any activity but enhance the activity of other components in the preparations? What are the components present in the urine of cow? Whether the urine contains microorganism, which are beneficial? Whether the degradation products from the urine are beneficial? To answer these questions the applicant obtained "Kamadhenu Arka" the urine distillate from "Go-Vigyana Anusandhana Kendra" Nagpur, India. This is the urine distillate suggested for drinking to improve the general health and sold and distributed in different size bottles. The applicants tested the urine on Luria agar and broth in sterile condition and did not notice any growth of microorganism. To test whether this is inhibitory to growth of different microorganism, *Escherichia coil* and *Mycobacterium smegmatis* were grown at different temperatures ranging from 20 to 40° C. in presence and in absence of the cow urine distillate, no significant difference in the colony count is noticed. Surprisingly, the same distillate enhanced the antibiotic action on these bacteria leading to this invention. The novelty of the invention lies in the fact revealed through precise experimentation that the enhancement action and its effectiveness is achievable only in the range of concentration which is literally in nano to micro molar levels. And when a higher concentration/dosage is used in the formulation or combinations the activity(ies) do not appear. That should be the reason for non-detection such a valuable potential of cow urine (Go-mutra). From million doses of annual antibiotics consumption goes waste as these could not be utilized or targeted to the infective organisms effectively due to various factors like efficient absorption, transportation to the target site, retention time, operation of efflux pump, metabolism etc. Thus, large portions of the drugs we apply are wasted and only a miniscule percentage is being targeted to the infective microbes. Also, the unutilized drug/antibiotic amount remains as a load in the body and environment acting as a selection pressure to facilitate emergence of drug resistance in parasites and their predominance, ultimately leading to failure of antibiotics against resistant infections. This also is responsible for side effects, illness and reduction in life expectancy being more acute in the older population. One of the ways, which has been feasible to reduce drug dosage, has been synergism between two therapeutic agents. However, if both have the antibiotic property, still the problem of continued selection pressure on microbes is likely to continue. So, the applicants thought of utilizing cow urine, which is not microbicidal but when present with a drug or active molecule, enhance its activity and availability (bioenhancers). This way, the selection pressure will be counter-balanced simultaneously reducing the dosage of antibiotics or drugs for minimizing the side effects, which has also high commercial importance.

The present invention was the result of planned experiments to provide a novel method for improving activity and bioavailability of antibiotics, drugs and other molecules using 'cow urine distillate' in different formulations.

The bioavailability of nutrients and enhancement antibiotics effect is relevant to human, plant as well as animal health and thus the compositions and methods of the invention are also intended to be used in agriculture and veterinary practice.

DESCRIPTION OF RELATED ART

Cow's urine (Go-mutra) can be considered as the most effective animal origin substance/secretion with the capacity of general health improvement but it does need substantiation through scientific experimentation. Thus, the applicants considered it worthwhile to scientifically look at this and define the molecular basis of the values through in vitro and in vivo assays. The applicants in the first instance probed whether it contained any drug facilitator elements since such a property would make it a highly useful natural substance. In recent days, use of 'piperine' as a bioavailability enhancer has been described (U.S. Pat. Nos. 5,616,593 and 5,972, 382). Till today thus, the known bioavailability enhancer documented is piperine and a series of inventions related to this compound have been described in the following prior arts.

OBJECTS OF THE INVENTION

The main objective is to provide new use of the bio-active fraction as a bio-enhancer and as a bioavailability facilitator.

In another objective of the invention is to provide method for improving activity and bioavailability of antibiotics, drugs and other molecules using active fraction from cow urine distillate.

Still another objective of the invention is to provide a process for the extraction of the active fraction form the cow urine.

SUMMARY OF THE INVENTION

The invention relates to new use of a known abundantly available cow urine distillate as an enhancer of antibiotic action on the target. The molecule of invention helps in the absorption of antibiotics across the cell membrane in animal cells, gram positive and gram negative bacteria Similar activities can also be obtained by using the distillate of the urine of cow at 40–50° C. and from the concentrate, which is lyophilized and dissolved for further use. Further the urine distillate from buffalo, camel, deer provides similar activity of bioavailability.

BRIEF DESCRIPTION OF THE ACCOMPANYING DRAWING

FIG. 1 represents HPLC characters of cow urine (Go-mutra) distillate

DETAILED DESCRIPTION OF THE INVENTION

Our emphasis here was to search a plentifully available material with bioenhancing action of higher potency. Additionally, a property that the applicants searched was the bioenhancement of a scarcely available anti-cancer natural agent 'taxol' (peclitaxel) which is produced in microscopic amounts by the Yew tree (*Taxus* spps.) and hence is always a limited molecule in availability. Cow urine distillate enhanced the killing activities of different antibiotics on bacteria. More important was the obvious enhancement in the cell division inhibitory activity against the breast cancer cell line MCF-7.

In an embodiment of the present invention a pharmaceutical composition comprising an effective amount of cow urine distillate as a bioavailability facilitator and a pharmaceutically acceptable additives selected from anticancer compounds, antibiotics, drugs, therapeutic and nutraceutic agents, ions and similar molecules which are targeted to the living systems.

In another embodiment, the cow urine distillate is used as bioavailability facilitator for anticancer therapy directly or in combination with anticancer molecules.

In still another embodiment, the cow urine distillate is used in antifungal therapy for fungal infections.

In yet another embodiment, the antifungals are azoles, clotrimazole, mystatin, amphotericin and similar materials.

In yet another embodiment, fungi covering infections are mycetial, candida, yeast or other fungicidal compounds.

In still another embodiment, the cow urine distillate is used in TB therapy including multi drug resistant tuberculosis in combination with isoniazid and other anti-tubercular agents.

In yet another embodiment, the bioavailability facilitator helps in transferring the compound across the membrane and for better effectivity on the target site.

In yet another embodiment, the antibiotics are Quinolones, fluoroquinolones like Nalidixic acid and others like Rifampicin, Tetracycline, ampicillin and similar compounds.

In yet another embodiment, the antibiotics, ions and similar compounds are isoniazid and hydrogen peroxide.

In yet another embodiment, the bioavailability facilitator helps the antibiotics and other molecules to act better on the target by increasing the effectivity.

In yet another embodiment, the living system may be bacteria, fungi or any living cells.

In yet another embodiment, the anti bacterial agents are selected from the group comprising Quinolones, Rifampicin, Tetracycline and ampicillin.

In yet another embodiment, the cow urine (Go-mutra) distillate is in the range between 0.001 µl/ml to 100 µl/ml.

In yet another embodiment, the lyophilized active fraction used is in the range between 0.1 µg/ml to 100 µg/ml.

In still another embodiment, the bioactive fraction enhances the activity of anti-bacterial agents, anti-cancer agents and anti-tuberculosis agents from 2 to 80 folds.

In yet another embodiment, the bioactive fraction enhances the activity of anti-bacterial agents from 2 to 80 folds.

In yet another embodiment, the anti bacterial agent is an anti-tuberculosis agent selected from isoniazid, pyrazinamide and other similar compounds.

In yet another preferred embodiment, the bioactive fraction enhances the activity of anti-tuberculosis agents from 2 to 20 folds.

In yet another embodiment of the invention, the anti-cancer agent is selected from group consisting of Paclitaxel (Taxol).

In yet another preferred embodiment of the invention, the bioactive fraction enhances the activity of anti-cancer agents from 2 to 20 folds.

The methodology followed by us for this screening included specifically designed bioassays as described below. The bacterial and fungal strains used in this invention were acquired commercially from Institute of Microbial Technology (IMTECH), Chandigarh which possessed corresponding properties of the ATCC strain mentioned.

1. Assay for Bio-Enhancement of Anti-Infective Agents
    a) The minimum inhibitory concentration (MIC) of antibiotic is determined against *Escherichia coli* (equivalent of ATCC 10536), *Bacillus subtilis* (equivalent of ATCC 6015) and *Mycobacterium smegmatis* (equivalent of ATCC 10231) in broth and disc diffusion assay.
    b) The antibiotics agents at concentrations ¼, ⅓, ½ and equal to MIC are added alone and in combination with the test compound at varying concentrations on disc and in broth to evaluate the comparative inhibition.
    c) These combination showing significant advantage or higher activity than antibiotic alone in terms of enhanced inhibition of bacterial growth (large inhibition zone in disc diffusion and affectivity of lower concentration in broth assay) are picked up for future testing.
    d) In broth assay the activity is quantified by counting number of viable cells in a given treatment and converted in fold enhancement by combination compared to antibiotic/drug alone in the killing percentage of cells.
    e) The pre-treatment assay followed to determine whether the compound is required along with antibiotic to enhance its activity or even its withdrawal after treatment or prior to antibiotic treatment would benefit. For this, the cells are treated with compound for 4 to 8 hours and then washed free of it by centrifugation and washing in sterile water. This was followed by treatment with antibiotic as in steps b to d.

2. Assay for Bio-Enhancement of Anti-Cancer Agents
    a) MCF-7 (Breast cancer commercial cell line obtained from National Center for Cell Sciences (NCCS), Pune) is inoculated at a density of about $0.1 \times 10^6$ cells in MEM medium in the wells of 24 well plate.
    b) This is replaced with fresh medium after 18 hours in each well.

c) The test component (s) is added at desired concentrations in different wells just after the medium replacement.
d) Observations are recorded on the cell count after 36 hours for which the following steps are required.
  i. The medium is removed from the wells.
  ii. The wells are rinsed with 1 ml PBS (Phosphate buffer saline).
  iii. To each well 500 µl of freshly prepared trypsin (0.1% in PBS) solution is added.
  iv. Trypsin solution is removed after 30 seconds and the plate is gently tapped till the cells are released from the plate surface.
  v. Fresh 1 ml of MEM growth medium is added and agitated with a pipette to obtain a cell suspension.
  vi. 10 µl of cell suspension is taken on the haemocytometer and a cover glass is placed over the counting chamber.
  vii. The number of viable cells is counted in 5 big squares and the readings are taken from 5 microscopic fields to determine the average.
  viii. The cell count (titer per ml) in the original sample is then calculated as average count $\times 10^3$.

Composition of Minimum Essential Medium (MEM): 100 ml

| | |
|---|---|
| MEM powder (Sigma - Aldrich, USA) = | 0.96 g |
| HEPES Buffer (Sigma - Aldrich, USA) = | 0.26 g |
| Sodium Bicarbonate = | 0.22 g |
| Penicillin G = | 10 mg |
| Streptomycin = | 20 mg |

-continued

| | |
|---|---|
| Gentamycin = | 5 mg |
| Foetal Calf Serum = | 15 ml |
| Foetal Calf Serum = | 15 ml |
| Distilled water = | 85 ml |

3. Bioavailability Tests through Biological Membrane
  a) Specially designed U-tubes of glass consisting of two components (opposite-L type) were used in which one open end of an L-shaped was tapered to fit within the untapered end of the other L-tube (FIG. 1).
  b) The membrane of goat gut (initial part) was stretched and fixed to act as the barrier between the two ends such that by joining the two L-tubes, a U-tube was made.
  c) Sterile distilled water was then filled in both the sides to equal height/level. The antibiotic/compound was added to the donor tube (tapered) and through spectrophotometer, the transfer of molecule was observed using UV and visible absorption maxima of the respective molecules by taking the OD at defined wavelengths.

EXAMPLES

In the next step of elucidation of the enhancer action, the applicants experimented with the killing activities of different antibiotics against the bacteria singly and in combination with the test component (cow urine distillate) following the method described above. These experiments are being described in the following examples. When the bacteria were grown in presence of the compound as such no significant killing was observed. In all the experiments the cow urine distillate concentration was kept at 1 µl/mL unless it is specifically mentioned.

Example 1

Cow Urine Distillate Mediated Enhancement in the Killing Action of Antibiotics Against Gram-negative Bacterium *Escherichia coli*

TABLE 1

| Antibiotics | Concentration µg/ml | Survival fraction of viable cells upon treatment with antibiotic alone | Survival fraction of viable cells upon treatment with antibiotic + cow urine distillate combination | *Fold enhancement in antibiotic activity |
|---|---|---|---|---|
| Rifampicin | 10 | 0.86 | 0.17 | 5.0 |
| Rifampicin | 30 | 0.05 | 0.007 | 7.1 |
| Ampicillin | 4 | 1.11 | 0.60 | 1.85 |
| Ampicillin | 6 | 0.09 | 0.02 | 4.50 |
| Ampicillin | 8 | 0.05 | 0.01 | 5.00 |

It was calculated as Survival fraction of viable cells upon treatment with antibiotic and cow urine distillate in combination/Survival fraction of viable cells upon treatment with antibiotic alone Example 2

Cow Urine Distillate Mediated Enhancement in the Killing Action of Antibiotics Against Gram-positive Bacterium *Bacillus subtilis*

TABLE 2

| Antibiotics | Concentration µg/ml | Survival fraction of viable cells upon treatment with antibiotic alone | Survival fraction of viable cells upon treatment with antibiotic + cow urine distillate combination | *Fold enhancement in antibiotic activity |
|---|---|---|---|---|
| Rifampicin | 0.005 | 1.1 | 0.28 | 5.5 |
| Rifampicin | 0.05 | 0.03 | 0.01 | 3.0 |

TABLE 2-continued

| Antibiotics | Concentration µg/ml | Survival fraction of viable cells upon treatment with antibiotic alone | Survival fraction of viable cells upon treatment with antibiotic + cow urine distillate combination | *Fold enhancement in antibiotic activity |
|---|---|---|---|---|
| Ampicillin | 0.1 | 1.00 | 0.3 | 3.3 |
| Ampicillin | 0.5 | 0.18 | 0.06 | 3.0 |

Example 3

Cow Urine (Go-mutra) Distillate Mediated Enhancement in the Killing Action of Antibiotics Against Bacterium *Mycobacterium smegmatis*

TABLE 3

| Antibiotics | Concentration µg/ml | Survival fraction of viable cells upon treatment with antibiotic alone | Survival fraction of viable cells upon treatment with antibiotic + cow urine distillate combination | *Fold enhancement in antibiotic activity |
|---|---|---|---|---|
| Rifampicin | 0.05 | 0.008 | 0.0001 | 80 |
| Rifampicin | 0.1 | 0.006 | 0.0036 | 1.5 |
| Ampicillin | 0.5 | 0.07 | 0.006 | 11.6 |

Example 4

Cow Urine Distillate Mediated Enhancement in the Killing Action of Izoniazid and Hydrogen Peroxide Against oxyR Mutant of Bacterium *Escherichia coli*. The Cow Urine Distillate Concentration is 0.001 µl/ml

TABLE 4

| | Concentration | Survival fraction of viable cells upon treatment with isoniazid/$H_2O_2$ alone | Survival fraction of viable cells upon treatment with a isoniazid/$H_2O_2$ + cow urine distillate combination | Fold enhancement in isoniazid/$H_2O_2$ activity |
|---|---|---|---|---|
| Isoniazid | 250 µg/ml | $7.5 \times 10^7$ | $0.99 \times 10^7$ | 7.5 |
| Hydrogen peroxide ($H_2O_2$) | 0.003% v/v | $7.14 \times 10^7$ | $1.2 \times 10^7$ | 5.9 |

The oxyR gene is required for the induction of a regulon of hydrogen peroxide-inducible genes in *Escherichia coli* (Christman M F, Storz G and Ames B N (1989) Oxy R, a positive regulator of hydrogen peroxide-inducible genes in *Escherichia coli* and *Salmonella typhimurium*, is homologous to a family of bacterial regulatory proteins (Proc. Natl. Acad. Sci. (USA). 86:3484–3488.). The mutants of these genes are sensitive to drugs like isoniazid and hydrogen peroxide, which produce free radicals, damaging the cellular systems. So the killing activities of these compounds are increased by 5 to 8 folds by cow urine.

Example 5

Cow Urine Distillate Mediated Enhancement in the Activity of Anti Cancerous Compounds. The Cow Urine Distillate Concentration is 1 µl/ml

TABLE 5

| Taxol Concentration µg/ml | Initial titre of viable cells | Final titre of viable cells upon treatment with taxol alone | Final titre of viable cells upon treatment with taxol + cow urine distillate |
|---|---|---|---|
| 0.001 | $0.9 \times 10^{-6}$ | $0.059 \times 10^6$ | $0.039 \times 10^6$ |
| 0.005 | $0.9 \times 10^{-6}$ | $0.042 \times 10^6$ | $0.032 \times 10^6$ |
| 0.01 | $0.9 \times 10^{-6}$ | $0.036 \times 10^6$ | $0.012 \times 10^6$ |

The applicants observed similar results of enhancement in the animal cell culture (cancerous cell line MCF-7 obtained from National Center for Cell Sciences (NCCS), Pune), in which the killing action of anti cancerous chemical 'Taxol' is increased. The components of cow urine distillate in our study help in transferring other compounds across the membrane thereby increasing the absorption in, irrespective of bacteria, animal and plant cell. This in-turn has immense importance for absorption of the drugs, pharmaceuticals, nutraceutical and other related compounds and ions by the cells.

Example 6

Bioenhancement of Antifungal Agent Clotrimazol by Bioactive Fraction Gm-IV. The Concentration of the Active Fraction is Kept at 10 µg/ml.

TABLE 6

| Treatment | Minimum inhibitory Concentration (MIC) in µg/ml | Fold enhancement |
| --- | --- | --- |
| Clotrimazol | 4.40 | 0.0 |
| Clotrimazol + Gm IV | 0.88 | 5.0 |

In other observations the compound cow urine distillate enhances the transport of antibiotics e.g. Rifampicin, Tetracycline, Ampicillin across the gut as well as artificial membrane. The enhancement in transport is approximately 2 to 7 folds.

Great emphasis now is being laid towards quality assurance of crude drugs from alternative sources widely used in the Indian system of medicine. The present invention enlarges the scope and use of the cow urine distillate in therapeutical and nutraceutical application.

Example 7

Development of powder form: For enhancing the utility and convenience of application of cow urine (Go-mutra), the applicants further fractionated to reach a solid form which is also free of the typical smell of cow urine distillate that it is more readily acceptable to the humans. For this purpose the urine distillate was fractionated as described by the following procedure:

Fractionation of a White Crystalline Solid from Cow Urine.

Step 1: Cow urine is collected aseptically in the stainless steel container directly from the cow, which is maintained in hygienic environment Step 2: Fifteen liters of cow urine is distilled continuously at 40–50 ° C. in glass distillation apparatus to obtain 10–12 liters of the distillate in 16 to 18 hours.

Step 3: The distillate is packed in surface sterilized plastic or glass container for further use Step 4: 200 ml of cow urine distillate was mixed with half the volume of methanol and extracted with hexane.

Step 5: The hexane fraction (Gm-I) was lyophilized and tested for similar activity as that of cow urine (Go-mutra).

Step 6: The aqueous fraction was extracted with ethyl acetate and the ethyl acetate fraction (Gm-II) was lyophilized and tested for similar activity as that of cow urine (Go-mutra).

Step 7: Further, aqueous fraction containing white precipitate was extracted with butanol and the butanol fraction (Gm-III) having pale yellow precipitate was lyophilized and tested for similar activity as that of cow urine (Go-mutra).

Step 8: The remaining aqueous fraction containing white crystalline precipitate (Gm-IV) was dried and tested for similar activity as that of cow urine (Go-mutra).

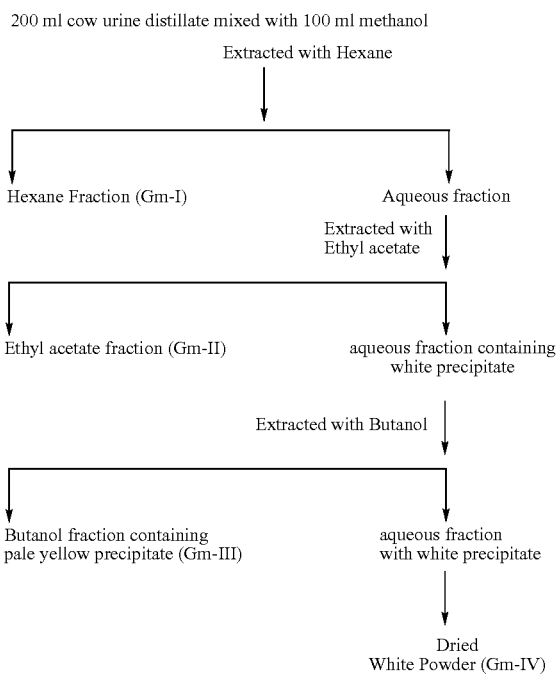

Scheme

The white powder (Gm-IV) that was obtained in the range of 10 to 20 grams per 100 ml of the distillate showed all the above activities as described for cow urine distillate at concentration 0.001 to 10 g/ml, with much more stability and being devoid of the unpleasant smell and hence was used as the advanced product of the invention. The novelty of the invention lies in the fact revealed through precise experimentation that the enhancement action and its effectiveness is achievable only in the range of concentration which is literally in nano to micro molar levels. And when a higher concentration/dosage is used in the formulation or combinations the activity(ies) do not appear.

Physical Characters of the Gm-IV Fraction

Color: White

Physical state: Solid Crystalline

Solubility: Water-soluble and mixture containing water

Melting point: Above 400° C.

Specific Gravity: 1.006

RF value in methanol: Chloroform (50:50) phase: 0.65

HPLC Characterization of Cow Urine (Go-mutra) Distillate

HPLC was performed on LC-8A Shimadzu HPLC with mobile phase water: acetonitrile (80:20), flow rate 10. m/min, UV detection at 275 nm and C-18 E MERCK (150×4 mm) column. Two major peaks (retention time 5.334 and 11.310 min) observed in the profile of cow urine (Go-mutra) distillate (FIG. 1).

Further characterization to test the chemical nature of the compound was performed through Feigl's test (In: E Stahl, Thin Layer Chromatography) which was positive indicating the presence of glycoside or sugar.

The novelty of the invention is that from cow urine (Go-mutra) distillate, a stable solid fraction could be isolated which is water soluble and devoid of the urine smell and can directly be used in any formulation.

The fraction Gm-IV also enhances the transport of antibiotics and vitamins across the mammalian gut membrane. The example describing the enhanced transport of rifampicin by the fraction Gm-IV is given below.

Example 8

Fraction Gm-IV of Cow Urine (Go-mutra) Distillate Mediated Enhancement in the Bioavailability Across the Biological Membrane (Rifampicin, 1 mg/ml and Fraction Gm-IV, 1.0 µg/ml).

TABLE 7

| Compound(s) in the donor tube | Wave length (nm) | OD measured as Absorbance (specific to the compound maxima) across the membrane in receiving tube after | | | | | |
|---|---|---|---|---|---|---|---|
| | | 1 hr | 2 hr | 3 hr | 4 hr | 5 hr | 6 hr |
| Rifampicin | $A_{340}$ | 0.0097 | 0.0214 | 0.0334 | 0.0771 | 0.0858 | 0.0910 |
| | $A_{475}$ | 0.0177 | 0.0284 | 0.0309 | 0.0412 | 0.0484 | 0.0496 |
| Rifampicin + Gm-IV | $A_{340}$ | 0.0525 | 0.0961 | 0.1353 | 0.1639 | 0.1919 | 0.1989 |
| | $A_{475}$ | 0.0502 | 0.0904 | 0.0793 | 0.0966 | 0.1157 | 0.1183 |

As cow urine (Go-mutra) distillate and the fraction Gm-IV, both shows enhanced membrane permeability by enhancing the antibiotics across the semi-permeable membrane and mammalian gut membrane, it can be assumed the above substances can be used for enhancing intestinal transport and transport of molecules across membranes of various biological functions including urinary/renal systems.

In all the experiments 1 to 5, the enhancing activity of the lyophilized product of the invention is found to have same enhancing activity like that of the distillate.

The invention can further be explained as follows:

1. The sample shows enhancement of bioavailability of rifampicin (antibiotic) and Vitamin B-12 across the mammalian gut membrane (Goat intestine was used) within 2 hours and it keeps increasing up to 4 hours.
2. It shows clear inhibition of ascorbic acid action to prevent oxidation of cut apple indicating that it probably enhances the isoniazid (INH) by oxidative mechanism that synergises the drug action of INH.
3. The distillate showed enhancement action for INH even at 10–50 thousand-fold dilution in the final volume of culture.
4. Still more interesting observation is that at 1 µl/ml the distillate showed enhancement in the activity of taxol by at least 5 folds. Further experiments in this direction have been taken up on priority.

The invention claimed is:

1. A process of preparing a white powder from cow urine distillate (GM-IV), said process comprising:
   a) mixing a volume of cow urine distillate with a volume of methanol, the volume of the methanol being half the volume of the cow urine distillate;
   b) extracting with hexane to produce a hexane fraction (GM-I) and an aqueous fraction;
   c) extracting the aqueous fraction with ethyl acetate to produce an ethyl acetate fraction (GM-II) and an aqueous fraction containing a white precipitate;
   d) extracting the aqueous fraction containing the white precipitate with butanol to produce a butanol fraction containing a pale yellow precipitate (GM-III) and an aqueous fraction with a white precipitate; and
   e) drying the aqueous fraction containing the white precipitate from step d) to form the white powder from cow urine distillate (GM-IV).

2. The process of claim 1, wherein the white powder from cow urine distillate is devoid of a cow urine smell.

3. The process of claim 1, wherein the white powder the following physical characteristics:
   a solid crystalline form, water solubility, a melting point above 400° C., a specific gravity of 1.006 and an RF value in methanol:chloroform (50:50) phase: 0.65.

4. The process of claim 1, wherein the white power has HPLC properties having two major peaks with retention times of 5.334 min and 11.310 min.

* * * * *